US010195125B2

(12) United States Patent
Pan et al.

(10) Patent No.: US 10,195,125 B2
(45) Date of Patent: *Feb. 5, 2019

(54) ORAL CARE COMPOSITION COMPRISING ZINC-LYSINE COMPLEX

(71) Applicant: Colgate-Palmolive Company, New York, NY (US)

(72) Inventors: Long Pan, Somerset, NJ (US); Jairajh Mattai, Piscataway, NJ (US); Shaotang Yuan, East Brunswick, NJ (US); James Masters, Ringoes, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/668,857

(22) Filed: Aug. 4, 2017

(65) Prior Publication Data

US 2017/0333311 A1 Nov. 23, 2017

Related U.S. Application Data

(63) Continuation of application No. 14/653,314, filed as application No. PCT/US2012/070498 on Dec. 19, 2012, now Pat. No. 9,757,316.

(51) Int. Cl.
*A61K 8/27* (2006.01)
*A61K 8/44* (2006.01)
*A61Q 11/00* (2006.01)
*A61Q 5/02* (2006.01)
*A61Q 19/10* (2006.01)
*A61Q 17/00* (2006.01)
*A61Q 15/00* (2006.01)
*A61Q 5/12* (2006.01)
*C07F 3/06* (2006.01)

(52) U.S. Cl.
CPC .............. *A61K 8/27* (2013.01); *A61K 8/44* (2013.01); *A61Q 5/02* (2013.01); *A61Q 5/12* (2013.01); *A61Q 11/00* (2013.01); *A61Q 15/00* (2013.01); *A61Q 17/005* (2013.01); *A61Q 19/10* (2013.01); *C07F 3/06* (2013.01); *A61K 2800/58* (2013.01); *A61K 2800/591* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 2,503,280 A | 4/1950 | Lockwood | |
| 2,507,088 A | 5/1950 | Bradley | |
| 2,527,686 A | 10/1950 | Sandberg | |
| 2,893,918 A | 7/1959 | Abramson | |
| 3,260,744 A | 7/1966 | Kankichi | |
| 3,320,174 A | 5/1967 | Rubinfeld | |
| 3,372,188 A | 3/1968 | Terence | |
| 3,535,421 A | 10/1970 | Briner | |
| 3,538,230 A | 11/1970 | Morton | |
| 3,678,154 A | 7/1972 | Briner | |
| 3,741,911 A | 6/1973 | Shane | |
| 3,862,307 A | 1/1975 | Giulio | |
| 3,937,807 A | 2/1976 | Haefele | |
| 3,941,818 A | 3/1976 | Abdel-Monem | |
| 3,959,458 A | 5/1976 | Agricola et al. | |
| 4,051,234 A | 9/1977 | Gieske et al. | |
| 4,316,824 A | 2/1982 | Pancheri | |
| 4,339,432 A | 7/1982 | Ritchey et al. | |
| 4,340,583 A | 7/1982 | Wason | |
| 4,487,757 A | 12/1984 | Kiozpeoplou | |
| 4,565,693 A | 1/1986 | Marschner | |
| 4,599,152 A | 7/1986 | Ashmead | |
| 4,684,528 A | 8/1987 | Godfrey | |
| 4,687,663 A | 8/1987 | Schaeffer | |
| 4,842,847 A | 6/1989 | Amjad | |
| 4,866,161 A | 9/1989 | Sikes et al. | |
| 4,885,155 A | 12/1989 | Parran, Jr. et al. | |
| 5,004,597 A | 4/1991 | Majeti et al. | |
| 5,061,815 A | 10/1991 | Leu | C07F 1/005 426/74 |
| 5,156,845 A | 10/1992 | Grodberg | |
| 5,188,821 A | 2/1993 | Gaffar et al. | |
| 5,192,531 A | 3/1993 | Gaffar et al. | |
| 5,470,876 A | 11/1995 | Proctor | A61K 8/46 514/20.7 |
| 5,504,055 A | 4/1996 | Hsu | |
| 5,643,559 A | 7/1997 | Eigen et al. | |
| 5,698,724 A | 12/1997 | Anderson et al. | |
| 5,707,679 A | 1/1998 | Nelson | |

(Continued)

FOREIGN PATENT DOCUMENTS

| | | | |
|---|---|---|---|
| CN | 101172956 | | 5/2008 |
| CN | 101172956 A | * | 5/2008 |

(Continued)

OTHER PUBLICATIONS

Machine translation of CN-101172956-A. (Year: 2017).*
Zhu Zhi-guo, Jin Zhongsheng, Liu Ju-tao, Liu Wei-ming, and Ma Degui. Synthesis and Crystal Structure of [Zn+ {H2N(CH2)4CH(NH2)COONa}2 SO4 ] • H20. Chinese Science Bulletin Sep. 1990, vol. 35 No. 18, pp. 1521-1525.
Machine translation of CN 101172956 A from Google.
Wang, "Research of synthesis process for new type laminate antihypertensives," Journal of Chemical Industry & Engineering, Apr. 2012, 33(2):38-40.

(Continued)

*Primary Examiner* — Michael P Cohen

(57) ABSTRACT

The invention provides a zinc-lysine complex having the formula $[Zn(C_6H_{14}N_2O_2)_2Cl]^+Cl^-$ having antibacterial and antiperspirant properties, together with personal care compositions comprising the complex, and methods of making and using these complexes and compositions.

11 Claims, 1 Drawing Sheet

(56) References Cited

U.S. PATENT DOCUMENTS

| | | | |
|---|---|---|---|
| 5,714,447 A | 2/1998 | Jones et al. | |
| 5,911,978 A | 6/1999 | Carr et al. | |
| 5,993,784 A | 11/1999 | Hill | |
| 6,121,315 A | 9/2000 | Nair et al. | |
| 6,156,293 A | 12/2000 | Jutila et al. | |
| 6,346,238 B1 | 2/2002 | Ascione et al. | |
| 6,607,711 B2 | 8/2003 | Pedersen | |
| 6,685,920 B2 | 2/2004 | Baig et al. | |
| 6,969,510 B2 | 11/2005 | Holerca et al. | |
| 8,067,627 B2 | 11/2011 | Newsome et al. | |
| 8,247,398 B2 | 8/2012 | Goel | |
| 9,572,756 B2 * | 2/2017 | Liu | A61K 8/27 |
| 9,675,823 B2 * | 6/2017 | Liu | A61K 8/46 |
| 9,757,316 B2 * | 9/2017 | Pan | A61K 8/27 |
| 9,763,865 B2 * | 9/2017 | Pan | A61K 8/27 |
| 9,775,792 B2 * | 10/2017 | Liu | A61K 8/27 |
| 9,913,784 B2 * | 3/2018 | Szewczyk | A61K 8/27 |
| 2003/0077332 A1 | 4/2003 | Godfrey | A61K 33/30 424/642 |
| 2004/0033916 A1 | 2/2004 | Kuzmin et al. | |
| 2004/0042978 A1 | 3/2004 | Embro | |
| 2004/0122088 A1 | 6/2004 | Newsome et al. | |
| 2004/0198998 A1 | 10/2004 | Holerca et al. | |
| 2006/0024252 A1 | 2/2006 | Esposito et al. | |
| 2007/0071698 A1 | 3/2007 | Doss | |
| 2009/0220444 A1 | 9/2009 | Teckenbrock et al. | |
| 2010/0021573 A1 | 1/2010 | Gonzalez et al. | |
| 2010/0266480 A1 | 10/2010 | Huang | |
| 2010/0330163 A1 | 12/2010 | Soparkar | |
| 2011/0076309 A1 | 3/2011 | Misner et al. | |
| 2011/0229536 A1 | 9/2011 | Kvitnitsky et al. | |
| 2013/0017240 A1 | 1/2013 | Porter et al. | |
| 2014/0170086 A1 | 6/2014 | Pan et al. | |

FOREIGN PATENT DOCUMENTS

| | | | |
|---|---|---|---|
| CN | 101172956 A | 5/2008 | C07C 229/26 |
| CN | 101606639 | 12/2009 | |
| CN | 102811698 | 12/2012 | |
| CN | 103156073 | 6/2013 | |
| CN | 103535536 | 1/2014 | |
| DE | 735096 | 5/1943 | |
| EP | 0083486 | 12/1982 | |
| EP | 0108937 | 5/1984 | |
| EP | 0508524 | 10/1992 | |
| EP | 0514553 | 11/1992 | |
| EP | 0842664 | 5/1998 | |
| EP | 1021158 | 7/2000 | |
| EP | 1064946 | 1/2001 | |
| EP | 1203575 | 5/2002 | |
| EP | 13193994 | 6/2003 | |
| EP | 1935395 | 6/2008 | |
| EP | 1529775 | 5/2011 | |
| FR | 2241301 | 3/1975 | |
| GB | 2052978 | 2/1981 | |
| GB | 2109685 | 6/1983 | |
| GB | 2243775 | 11/1991 | |
| JP | S57-158724 | 9/1982 | |
| JP | 2000-191416 | 7/2000 | |
| JP | 2004175790 | 6/2004 | |
| JP | 2009084201 | 4/2009 | |
| JP | 2010132639 | 6/2010 | |
| WO | WO86/00004 | 1/1986 | |
| WO | WO9917735 | 4/1999 | |
| WO | WO199917735 | 4/1999 | |
| WO | WO0169087 | 9/2001 | |
| WO | WO2004054531 | 7/2004 | |
| WO | WO2004/064536 | 8/2004 | |
| WO | WO2007063507 | 6/2007 | |
| WO | WO2011053291 | 5/2011 | |
| WO | WO2011/088199 | 7/2011 | |
| WO | WO2011/123123 | 10/2011 | |
| WO | WO2014/098813 | 6/2014 | |
| WO | WO2014/098814 | 6/2014 | |
| WO | WO2014/098818 | 6/2014 | |
| WO | WO2014/098819 | 6/2014 | |
| WO | WO2014/098821 | 6/2014 | |
| WO | WO2014/098822 | 6/2014 | |
| WO | WO2014/098824 | 6/2014 | |
| WO | WO2014/099164 | 6/2014 | |
| WO | WO2014/099165 | 6/2014 | |
| WO | WO2014/099166 | 6/2014 | |
| WO | WO2014/099167 | 6/2014 | |
| WO | WO2014098825 | 6/2014 | |
| WO | WO2014098826 | 6/2014 | |
| WO | WO2014098828 | 6/2014 | |
| WO | WO2014098829 | 6/2014 | |
| WO | WO2014099039 | 6/2014 | |
| WO | WO2014099226 | 6/2014 | |
| WO | WO2014204439 | 12/2014 | |

OTHER PUBLICATIONS

Annonymous, "Zinc Lauryl Ether Sulphate, A New Approach to Skincare,", Apr. 2004. Retrieved from Internet, http://www.erwebhosting.it/zsi/repository/Zinc%20Lauryl%20Ether%20Sulphate,%20A%20new%20approach%20to%20skin%20care.pdf, Retrieved Sep. 26, 2013.

Deschaume et al., "Interactions of aluminum hydrolytic species with biomolecules," New Journal of Chemistry, 2008, 32:1346-1353.

European Food Safety Authority, "Scientific Opinion on the safety and efficacy of tetra-basic zinc chloride for all animal species," EFSA Journal, 2012, 10(5):2672.

Hartwell et al., "Preparation and characterization of tyrosine and lysine metal chelate polyesters and polyamides", J. of the American Chem. Society, Mar. 1970, 92(5):1284-1289.

International Search Report and Written Opinion for International Application No. PCT/US2012/070489 dated Oct. 22, 2013.
International Search Report and Written Opinion for International Application No. PCT/US2012/070492 dated Oct. 22, 2013.
International Search Report and Written Opinion for International Application No. PCT/US2012/070498 dated Sep. 4, 2013.
International Search Report and Written Opinion for International Application No. PCT/US2012/070501 dated Oct. 21, 2013.
International Search Report and Written Opinion for International Application No. PCT/US2012/070505 dated Nov. 20, 2013.
International Search Report and Written Opinion for International Application No. PCT/US2012/070506 dated Oct. 14, 2013.
International Search Report and Written Opinion for International Application No. PCT/US2012/070513 dated Oct. 14, 2013.
International Search Report and Written Opinion for International Application No. PCT/US2012/070521 dated Sep. 30, 2013.
International Search Report and Written Opinion for International Application No. PCT/US2012/070525 dated Sep. 27, 2013.
International Search Report and Written Opinion for International Application No. PCT/US2012/070528 dated Sep. 30, 2013.
International Search Report and Written Opinion for International Application No. PCT/US2012/070534 dated Sep. 26, 2013.
International Search Report and Written Opinion for International Application No. PCT/US2012/070537 dated Oct. 11, 2013.
International Search Report and Written Opinion for International Application No. PCT/US2013/046268 dated Apr. 22, 2014.
International Search Report and Written Opinion for International Application No. PCT/US2013/050845 dated Aug. 13, 2014.
International Search Report and Written Opinion for international Application No. PCT/US2013/068852 dated Nov. 10, 2014.
International Search Report and Written Opinion for International Application No. PCT/US2013/068854 dated Oct. 20, 2014.
International Search Report and Written Opinion for International Application No. PCT/US2013/068859 dated Aug. 4, 2014.
International Search Report and Written Opinion for International Application No. PCT/US2013/068860 dated Oct. 22, 2014.
International Search Report and Written Opinion for International Application No. PCT/US2013/070932 dated Jul. 24, 2014.
International Search Report and Written Opinion for International Application No. PCT/US2014/042947 dated Aug. 22, 2014.

(56) References Cited

OTHER PUBLICATIONS

International Search Report and Written Opinion for International Application No. PCT/US2014/042948 dated Aug. 26, 2014.
International Search Report and Written Opinion for International Application No. PCT/US2014/043051 dated Feb. 18, 2015.
Kondrot, "Importance of Zinc," http://www.healingtheeye.com/Articles/zinc.html Feb. 21, 2012.
Liang et al., "In vitro scratch assay: a convenient and inexpensive method for analysis of cell migration in vitro," Nature Protocols, 2007, 2(2):329-333.
Liu et al., "The research on zinc coordination No. 5 odd structure in zinc complex with L-lysine," J. Molecular Science, 2000, 16(2):114-117, abstract only in English.
Lu et al., "Albumin as a zinc carrier: properties of its high-affinity zinc-binding site", Biochem. Soc. Trans., 2008, 36:1317-1321.
Lynch, "Zinc in the mouth, its interactions with dental enamel and possible effects on caries: a review of the literature," Int. Dent. J., Aug. 2011, Suppl 3:46-54.
Mavromichalis et al., "Growth-promoting efficacy of pharmacological doses of tetrabasic zinc chloride in diets for nursery pigs," Canadian Journal of Animal Science, pp. 387-391, Jan. 2001.
McAuliffe et al., "Metal complexes of sulphur-containing amino acids," Inorganica Chimica Acta Reviews, Dec. 1972, 6:103-121.
Moore et al., "Antibacterial activity of gutta-percha cones attributed to the zinc oxide component," Oral Surgery, 1982, 53:508-517.
Mosmann, "Rapid colorimetric assay for cellular growth and survival: Application to proliferation and cytotoxicity assays," J. Immunol. Methods, 1983, 65:55-63.
Pashley et al. Dentin permeability effects of desensitizing dentifrices in vitro. J Periodontol. 1984;55(9):522-525.
Prasad, "Zinc:role in immunity, oxidative stress and chronic inflammation," Current Opinion in Clinical Nutrition and Metabolic Care. 2009, 12:646-652.
Rigano, L., Zinc Lauryl Ether Sulphate—A New Approach to Skin Care, SOFW Journal, Apr. 2004, 128:26-33.
Schmetzer et al., "Wulfingite, $\epsilon$-Zn(OH)$_2$, and simonkolleite, Zn$_5$(OH)$_8$Cl$_2$•H$_2$O, two new minerals from Richelsdorf, Hesse, F.R.G.," N Jb Miner Mh., Apr. 1985, pp. 145-154.
Seil et al. "Antibacterial effect of zinc oxide nanoparticles combined with ultrasound," Nanotechology,2012, 23:495101.
Soderling et al., "Betaine-containing toothpaste relieves subjective symptoms of dry mouth," Acta Odontol. Scand., Apr. 1998, 56(2):65-9.
Stewart et al., "Interdomain zinc site on human albumin," PNAS, 2003, 100(7):3701-3706.
Tian et al., "Using DGGE profiling to develop a novel culture medium suitable for oral microbial communities," Molecular Oral Microbiology, 2010, 25(5):357-367.
Twetman et al., 2003, "Caries-preventative effect of fluoride toothpaste a systematic review," Acta Odontol Scand., Dec. 2003, 61(6):347-55.
Wachi et al., "Antibacterial compsn. Zinc oxide—solubilized by amino acid, amino acid hydrochloride and/or amino acid alkali metal salt," Sep. 1982, vol. 1982(45).
Wallhausser et al., "Antimicrobial Preservatives in Europe: Experience with preservatives used in pharmaceuticals and cosmetics," Develop. Biol. Standard, 1974, 24:9-28.
Yao et al., "An investigation of zirconium(IV)-glycine(CP-2) hybrid complex in bovine serum albumin protein matrix under varying conditions," J. of Materials Chemistry, 2011, 21:19005-19012.
Yousef et al., "In vitro antibacterial activity and minimum inhibitory concentration of zinc oxide and nano-particle zinc oxide against pathogenic strains," J. of Health Sciences, 2012, 2(4):38-42.
Zhu et al. "Synthesis and Crystal Structure of [Zn+{H2N(CH2)4CH(NH2)COONa}2SO4-] •H20," Chinese Science Bulletin, Sep. 1990, 35(18):1521-1525.

* cited by examiner

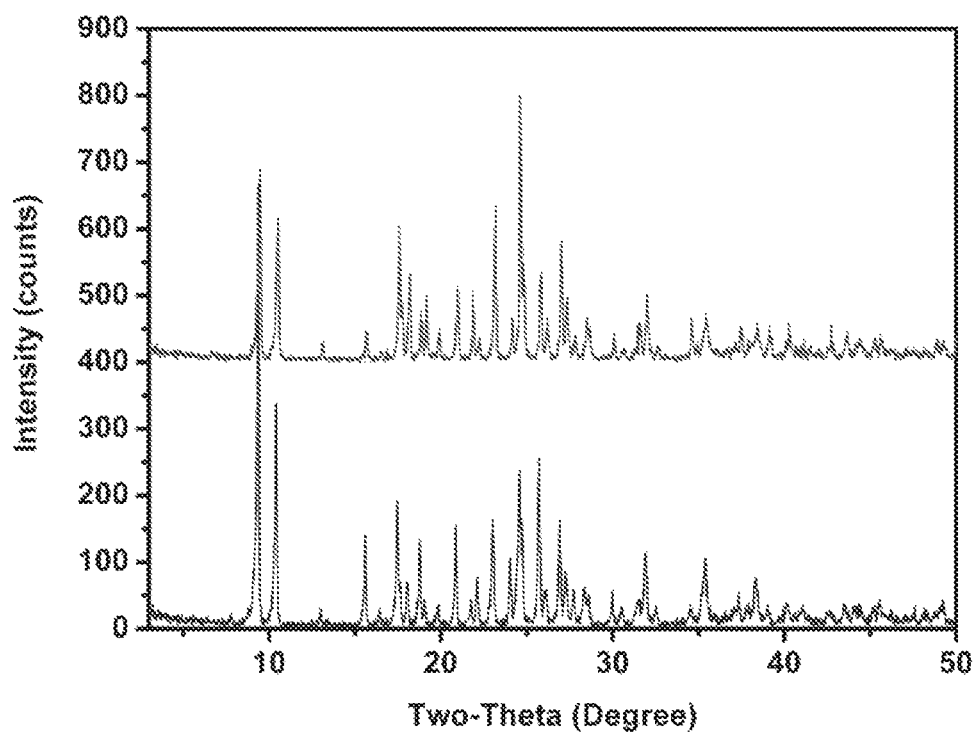

ORAL CARE COMPOSITION COMPRISING ZINC-LYSINE COMPLEX

CROSS-REFERENCE TO RELATED APPLICATIONS

This application is Continuation Application filed under 35 U.S.C. § 111 of U.S. application Ser. No. 14/653,314, filed on Jun. 18, 2015, which is a United States National Stage Application under 35 U.S.C. § 371 of International Application PCT/US2012/070498, filed on Dec. 19, 2012, the contents of each of which are hereby incorporated by reference in their entireties.

BACKGROUND OF THE INVENTION

Antiperspirants based on aluminum or aluminum/zirconium salts are known. These materials function as antiperspirants by plugging pores thereby blocking sweat release. Antiperspirant compositions containing aluminum or aluminum-zirconium salts tend to exhibit polymerization of these salts over time, forming species with molecular weights ranging from about 500 to about 500,000 g/mol. In general, lower molecular weight species have greater antiperspirant effect than higher molecular weight species. Without being bound by theory, it is believed that the smaller molecules more readily and more effectively occlude sweat pores, thereby producing the desired antiperspirant effect. Maintaining a relatively low molecular weight and avoiding excessive polymerization enhances the antiperspirant effect and moreover lowers the amount of antiperspirant salt which necessary to control perspiration.

Underarm deodorants control odor by eliminating the bacteria that cause odor. Conventional antiperspirant salts tend to be acidic in aqueous solution, a property which makes them effective bacteriocides, thereby providing a deodorant benefit, but which can also cause skin irritation.

There is a need for additional antiperspirant active agents that provide molecular weight complexes of a size capable of plugging pores to block sweat, that provide deodorant/antibacterial efficacy, and that are less irritating to the skin than the acidic salts in conventional antiperspirants.

BRIEF SUMMARY OF THE INVENTION

The invention provides a zinc-lysine complex, sometimes referred to herein as ZLC, formed from a mixture of zinc oxide and lysine hydrochloride. The chemical structure of ZLC is $[Zn(C_6H_{14}N_2O_2)_2Cl]^+Cl^-$. This salt has key features (e.g., conductivity, hydrolysis reaction and protein flocculation) which make it competitive with commercial antiperspirant salts.

Like the existing aluminum or aluminum-zirconium antiperspirant salts, ZLC forms precipitates under sweat conditions that can plug the pores and block sweat release. In the presence of protein, the ZLC will flocculate and plug the sweat glands. As the amount of water increases, rather than going into or remaining in solution as the solution becomes more dilute, as would typically be the case for an ionic complex, the ZLC complex hydrolyzes, to provide a relatively insoluble zinc oxide precipitate, thereby permitting further plugging of the pores and/or controlled deposition of zinc oxide on the skin. The zinc is antibacterial, and so in addition to providing a precipitate which blocks sweat release from the pores, it provides a deodorant benefit by reducing odor-causing bacteria. Finally, the ZLC may be provided in a formulation which is approximately pH neutral, which is closer in pH to skin than the currently-used antiperspirant salts, or current deodorant formulations.

The invention thus provides ZLC per se, as well as personal care products that deliver ZLC to the skin, and methods of making and using ZLC. In one embodiment, the invention provides antiperspirant or deodorant compositions that comprise ZLC. As the ZLC antibacterial properties, the invention also encompasses other personal care compositions for application to the skin, for example hand soaps or body washes, comprising a ZLC, e.g., any of Complex 1, et seq. and/or precursors thereof. The invention further provides methods of reducing sweat comprising applying the composition to skin, and methods of killing bacteria comprising contacting the bacteria with the composition.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein FIG. 1 depicts the X-ray powder diffraction (PXRD) of laboratory synthesized ZLC powder (top), and PXRD of ZLC single crystal bottom.

DETAILED DESCRIPTION OF THE INVENTION

The following description of the preferred embodiment(s) is merely exemplary in nature and is in no way intended to limit the invention, its application, or uses.

The invention therefore provides, in a first embodiment, a zinc-lysine complex having the formula $[Zn(C_6H_{14}N_2O_2)_2Cl]^+Cl^-$ (sometimes referred to herein as "ZLC"), e.g., 1.1. Complex 1 wherein the complex is formed from a mixture of zinc oxide and lysine hydrochloride, e.g., in a molar ratio of ZnO:Lysine.HCl of 1:1 to 1:3, e.g., about 1:2.
1.2. Complex 1, or 1.1 in crystalline form.
1.3. Any of the foregoing complexes in the form of a hydrate.
1.4. Any of the foregoing complexes in the form of a hydrate having the formula $[Zn(Lysine)_2Cl]^+Cl^-.2H_2O$.
1.5. Any of the foregoing complexes having $C_{12}H_{32}N_4O_6Cl_2Zn$ with molecular weight of 464.4 g/mol.
1.6. Any of the foregoing complexes in the form of approximately cubic crystals.
1.7. Any of the foregoing complexes having a structure wherein the Zn cation is coordinated by two lysine ligands with two nitrogen atoms from alpha $NH_2$ groups of the two lysine ligands and two oxygen atoms from carboxylic groups of the two lysine ligands in an equatorial plane, having a distorted square-pyramidal geometry with the apical position occupied by a chlorine atom, to form a positive cation moiety, with which a chloride anion is combined to form an ionic salt.
1.8. Any of the foregoing complexes having a powder X-ray diffraction pattern substantially corresponding to one of the two patterns depicted in FIG. 1. By "substantially corresponding" is meant a correspondence indicating to one of skill in the art that the crystal is the same as or is predominantly composed of the ZLC crystal, e.g., based on the overall pattern of relative intensity and spacing of the peaks, taking into account instrumental and sample variation, e.g., variations in the wavelength and intensity of the x-ray source and the purity of the sample.

1.9. Any of the foregoing complexes when crystalized from aqueous ethanol.

1.10. Any of the foregoing complexes which forms a zinc oxide precipitate upon increasing dilution with water.

In a further embodiment, the invention provides a personal care composition (Composition 2) for application to the skin which comprises ZLC, e.g., any of Complex 1, et seq., as described above, in combination with a cosmetically acceptable carrier. For example, the invention provides 2.1. Composition 2 comprising zinc oxide and lysine hydrochloride in a molar ratio of ZnO:Lysine.HCl of 1:1 to 1:3, e.g., about 1:2.

2.2. Any of the foregoing compositions wherein the ZLC is crystallized from ethanol.

2.3. Any of the foregoing compositions wherein ZLC is formed, in whole or in part, in situ from zinc oxide and lysine hydrochloride.

2.4. Any of the foregoing compositions wherein, upon dilution with water, the ZLC provides a zinc oxide precipitate.

2.5. Any of the foregoing compositions which, upon use, provides a zinc oxide precipitate to the skin.

2.6. Any of the foregoing compositions comprising ZLC in an amount of 0.05 to 40% by weight of the composition.

2.7. Any of the foregoing compositions, wherein a total amount of zinc present in the composition is 0.05 to 10% by weight.

2.8. Any of the foregoing compositions, wherein the cosmetically acceptable carrier comprises less than 10% water, e.g., less than 5% water, e.g., is substantially anhydrous.

2.9. Any of the foregoing compositions wherein the cosmetically acceptable carrier comprises one or more ingredients selected from water-soluble alcohols (such as $C_{2-8}$ alcohols including ethanol); glycols (including propylene glycol, dipropylene glycol, tripropylene glycol and mixtures thereof); glycerides (including mono-, di- and triglycerides); medium to long chain organic acids, alcohols and esters; surfactants (including emulsifying and dispersing agents); additional amino acids; structurants (including thickeners and gelling agents, for example polymers, silicates and silicon dioxide); emollients; fragrances; and colorants (including dyes and pigments).

2.10. Any of the foregoing compositions, wherein the composition is an antiperspirant and/or deodorant, e.g., an antiperspirant stick, an aerosol antiperspirant spray, or a liquid roll-on antiperspirant; or is a body wash, a shower gel, a bar soap, a shampoo, a hair conditioner, a toothpaste, a dentifrice, or a mouth wash.

In a further embodiment, the invention provides an oral care composition (Composition 3) for application to the oral cavity which comprises ZLC, e.g., any of Complex 1, et seq., as described above, in combination with an orally acceptable carrier. For example, the invention provides 3.1. Composition 3 comprising zinc oxide and lysine hydrochloride in a molar ratio of ZnO:Lysine.HCl of 1:1 to 1:3, e.g., about 1.2

3.2. Any of the foregoing compositions wherein the ZLC is crystallized from ethanol.

3.3. Any of the foregoing compositions wherein ZLC is formed, in whole or in part, in situ from zinc oxide and lysine hydrochloride.

3.4. Any of the foregoing compositions wherein, upon dilution with water, the ZLC provides a zinc oxide precipitate.

3.5. Any of the foregoing compositions which, upon use, provides a zinc oxide precipitate to the skin.

3.6. Any of the foregoing compositions comprising ZLC in an amount of 0.05 to 40% by weight of the composition.

3.7. Any of the foregoing compositions, wherein a total amount of zinc present in the composition is 0.05 to 10% by weight.

3.8. Any of the foregoing compositions, wherein the cosmetically acceptable carrier comprises less than 10% water, e.g., less than 5% water, e.g., is substantially anhydrous.

The invention further provides methods of reducing perspiration comprising applying an antiperspirant effective amount of any of Composition 2, et seq. to the skin, methods of reducing body odor comprising applying a deodorant-effective amount of any of Composition 2, et seq. to the skin, and methods of killing bacteria comprising contacting the bacteria with an antibacterially effective amount of a ZLC, e.g., any of Complex 1, et seq. for example contacting with e.g., any of Composition 2, et seq.

The invention further provides a method of making a composition comprising ZLC, e.g., any of Complex 1, et seq. comprising combining zinc oxide and lysine hydrochloride in aqueous solution, and optionally adding this mixture to ethanol and isolating the crystalline precipitate thus obtained.

The invention further provides (i) the use of a ZLC, e.g., any of Complex 1, et seq., to kill bacteria, reduce perspiration, and/or reduce body odor; (ii) the use of a ZLC, e.g., any of Complex 1, et seq., in the manufacture of a composition to kill bacteria, reduce perspiration, and/or reduce body odor; and (iii) ZLC, e.g., any of Complex 1, et seq., for use in killing bacteria, reducing perspiration, and/or reducing body odor.

It will be understood that, although the ZLC may be primarily in the form of a complex, there may be some degree of equilibrium with zinc oxide and lysine hydrochloride precursor materials, so that the proportion of material which is actually in complex compared to the proportion in precursor form may vary depending on the precise conditions of formulation, concentration of materials, presence or absence of water, presence or absence of other charged molecules, and so forth.

ZLC, e.g., any of Complex 1, et seq., can be incorporated into a suitable base, for example a stick, roll-on, spray or aerosol for application to the underarm. Following application, the ZLC in the presence of charged molecules such as proteins found on the skin, the ZLC will flocculate, forming plugs which block sweat release. Additional water from sweat can moreover dilute the formulation, causing the complex to decompose, resulting in precipitation of zinc oxide, which can reduce sweat and odor as described above. Similarly, if the ZLC is provided in a hand soap or body wash base, the dilution of the ZLC upon washing results in a thin deposition of zinc oxide on the skin, providing an antibacterial effect.

As used herein, the term antiperspirant can refer to any material that can form a plug in a pore to reduce sweating, or antiperspirant refers to those materials classified as antiperspirants by the Food and Drug Administration under 21

CFR part 350. Antiperspirants may also be deodorants, particularly in the case of this invention, as zinc has antibacterial properties and can reduce odor-causing bacteria on the skin.

The composition can include the ZLC, any of Complex 1, et seq. and/or precursors thereof, for example zinc oxide and lysine hydrochloride. In one embodiment, the ZLC is prepared at room temperature by mixing the precursors in an aqueous solution. The in situ formation provides ease of formulation. The precursors can be used instead of first having to form the ZLC. In another embodiment, the water permitting formation of the ZLC, e.g., any of Complex 1, et seq. from the precursor comes from sweat that comes into contact with the composition after application.

In certain embodiments, the amount of ZLC, e.g., any of Complex 1, et seq. in the composition of the invention, e.g., any of Compositions 2, et seq., is 0.05 to 40% by weight of the composition. In certain embodiments, precursors, e.g., zinc oxide and lysine hydrochloride, are present in amounts such that when combined into the ZLC, e.g., any of Complex 1, et seq., the ZLC, e.g., any of Complex 1, et seq. would be present in an amount of 0.05 to 10% by weight of the composition. In either of these embodiments, the amount of the ZLC, e.g., any of Complex 1, et seq. can be varied for the desired purpose, such as an antibacterial agent or as an antiperspirant. In other embodiments, the amount of the ZLC, e.g., of Complex 1, et seq. is at least 0.1, at least 0.2, at least 0.3, at least 0.4, at least 0.5, at least 1, at least 2, at least 3, or at least 4 up to 10% by weight of the composition. In other embodiments, the amount of the ZLC, e.g., any of Complex 1, et seq. is less than 9, less than 8, less than 7, less than 6, less than 5, less than 4, less than 3, less than 2, less than 1, less than 0.5 to 0.05% by weight of the composition. In other embodiments, the amounts are 0.05 to 5%, 0.05 to 4%, 0.05 to 3%, 0.05 to 2%, 0.1 to 5%, 0.1 to 4%, 0.1 to 3%, 0.1 to 0.5 to 5%, 0.5 to 4%, 0.5 to 3%, or 0.5 to 2% by weight of the composition.

In some embodiments, the total amount of zinc in the composition is 0.05 to 10% by weight of the composition. In other embodiments, the total amount of zinc is at least 0.1, at least 0.2, at least 0.3, at least 0.4, at least 0.5, or at least 1 up to 8% by weight of the composition. In other embodiments, the total amount of zinc in the composition is less than 5, less than 4, less than 3, less than 2, or less than 1 to 0.05% by weight of the composition.

In certain embodiments, the composition is anhydrous. By anhydrous, there is less than 5% by weight water, optionally less than 4, less than 3, less than 2, less than 1, less than 0.5, less than 0.1 down to 0% by weight water.

When provided in an anhydrous composition, precursors, e.g., zinc oxide and lysine hydrochloride, will not significantly react to form the ZLC, any of Complex 1, et seq. When contacted with a sufficient amount of water, which can be in the form of sweat, the precursors will then react to form the ZLC, e.g., any of Complex 1, et seq. The ZLC, any of Complex 1, et seq. when introduced into a sweat duct will flocculate with protein and/or hydrolyze with water and/or sweat to form a precipitate to block the sweat duct.

In certain embodiments, the ZLC, e.g., any of Complex 1, et seq, can have a conductivity of greater than 8000, optionally greater than 9000, greater than 10,000, or greater than 12,000 µS/cm.

The composition can be any type of composition. In certain embodiments, the composition is any composition in which it is desired to include an antibacterial agent for application to the skin. Examples of such compositions include, but are not limited to, personal care compositions, antiperspirants, deodorants, body washes, shower gels, bar soaps, shampoo, hair conditioners, cosmetics.

The carrier represents all other materials in the composition other than the ZLC, e.g., any of Complex 1, et seq. or the zinc oxide and amino acid hydrohalide. The amount of carrier is then the amount to reach 100% by adding to the weight of the ZLC, e.g., any of Complex 1, et seq. or the zinc oxide and amino acid hydrohalide.

For antiperspirant/deodorant compositions, the carrier can be any carrier that is used for antiperspirants/deodorants. The carrier can be in the form of a stick, a gel, a roll-on, or an aerosol. For stick formulations, the carrier may include oils and/or silicones and gelling agents. An example of a formulation can be found in US2011/0076309A1, incorporated by reference herein.

Optional ingredients that can be included in an antiperspirant and/or deodorant formulation of the compositions of the invention include solvents; water-soluble alcohols such as $C_{2-8}$ alcohols including ethanol; glycols including propylene glycol, dipropylene glycol, tripropylene glycol and mixtures thereof; glycerides including mono-, di- and tri-glycerides; medium to long chain organic acids, alcohols and esters; surfactants including emulsifying and dispersing agents; amino acids including glycine; structurants including thickeners and gelling agents, for example polymers, silicates and silicon dioxide; emollients; fragrances; and colorants including dyes and pigments. If desired, an antiperspirant and/or deodorant agent additional to the ZLC, e.g., any of Complex 1, et seq. can be included, for example an odor reducing agent such as a sulfur precipitating agent, e.g., copper gluconate, zinc gluconate, zinc citrate, etc.

The antiperspirant compositions can be formulated into topical antiperspirant and/or deodorant formulations suitable for application to skin, illustratively a stick, a gel, a cream, a roll-on, a soft solid, a powder, a liquid, an emulsion, a suspension, a dispersion or a spray. The composition can comprise a single phase or can be a multi-phase system, for example a system comprising a polar phase and an oil phase, optionally in the form of a stable emulsion. The composition can be liquid, semi-solid or solid. The antiperspirant and/or deodorant formulation can be provided in any suitable container such as an aerosol can, tube or container with a porous cap, roll-on container, bottle, container with an open end, etc.

The compositions can be used in a method to reduce sweating by applying the composition to skin. In certain embodiments, the application is to axilla. Also, the compositions can be used to kill bacteria by contacting bacteria with the composition. For example, in one embodiment, the combination of the amino acid or amino acid hydrohalide with the zinc oxide increases the availability of zinc ions, which can then kill bacteria and reduce sweat.

Thus the invention provides (i) a method for controlling perspiration comprising applying to skin an antiperspirant effective amount of a formulation of any embodiment embraced or specifically described herein, e.g., any of Compositions 1 et seq.; and (ii) a method for controlling odor from perspiration comprises applying to skin a deodorant effective amount of a formulation of any embodiment embraced or specifically described herein, e.g., any of Compositions 1 et seq.

Unless stated otherwise, all percentages of composition components given in this specification are by weight based on a total composition or formulation weight of 100%.

Unless otherwise specifically identified, the ingredients for use in the compositions and formulations of the present invention are preferably cosmetically acceptable ingredients. By "cosmetically acceptable" is meant suitable for use in a formulation for topical application to human skin. A cosmetically acceptable excipient, for example, is an excipient which is suitable for external application in the amounts and concentrations contemplated in the formulations of this invention, and includes for example excipients which are "Generally Recognized as Safe" (GRAS) by the United States Food and Drug Administration.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the invention extends to the product of the combination of the listed ingredients.

EXAMPLE 1

Synthesis and Characterization of Zinc-lysine Complex ZLC

The general reaction for formation of ZLC is as follows:

$$ZnO + 2(Lysine.HCl) \rightarrow [Zn(Lysine)_2Cl]^+Cl^-.2H_2O \text{ (ZLC)}$$

A 2:1 molar ratio of ZnO:Lysine.HCl suspension is prepared with stirring at room temperature for about 12 hours. The mixture is centrifuged. 1 ml of supernatant is transferred into an NMR tube. The NMR tube is then placed in a closed test tube filled with ethanol for crystal growth. A number of colorless, cubic crystals are formed after a week. The crystal structure of ZLC crystal is determined by single crystal X-ray diffraction. ZLC has an empirical formula as 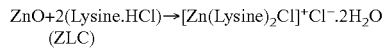 with molecular weight of 464.44 g/mol. In this complex, Zn cation is coordinated by two two lysine ligands with two N atoms from $NH_2$ groups and O atoms from carboxylic groups in an equatorial plane. It displays a distorted square-pyramidal geometry with the apical position occupied by a Cl atom. This structure gives rise to a positive cation moiety, to which a Cl anion is combined to form an ionic salt.

Laboratory scale-up synthesis of pure ZLC powder: 2 mole of LysineHCl is dissolved in 1000 ml DI water with stirring at room temperature, 1 mole of solid ZnO is added slowly to the LysineHCl solution with stirring and the stirring is continued at RT overnight (about 12 hours). The suspension solution is centrifuged at high speed for 15 mins. The supernatant is slowly poured into EtOH. A precipitate is formed immediately. Approximately 5-8 ml EtOH is needed to get 1 g powder. The EtOH solvent with powder is filtered, and an off-white powder is obtained. The powder is placed in a 50° C. oven for drying and an 88% yield of product is obtained, PXRD confirms the purity of ZLC powder compared to ZLC crystal (FIG. 1). In this example, the ZLC is crystallized by using ethanol as an antisolvent. Any antisolvent can be used. Optionally, the solution can be spray dried.

EXAMPLE 2

Mechanisms of Sweat Reduction

Hydrolysis reaction: A 185 mg/ml ZLC solution is prepared and diluted several-fold and aged in a 37° C. oven over 5 hours for turbidity studies. A white precipitate forms as the solution is diluted. Turbidity of the solutions is measured using a nephelometer, results being given in nephelometric turbidity units (NTU). Table 1 shows a comparison of pH and turbidity before and after aging, showing an increase in turbidity with dilution and with aging:

TABLE 1

|  | 185 mg/ml | 92.5 mg/ml | 46.25 mg/ml | 23.125 mg/ml | 11.56 mg/ml | 5.78 mg/ml |
|---|---|---|---|---|---|---|
| initial pH | 6.8 | 7 | 7.4 | 7.7 | 7.8 | 8 |
| initial turbidity (NTU) | 4.7 | 2.8 | 1.5 | 0.7 | 14.8 | 40.1 |
| pH after aging | 6.8 | 7 | 7.4 | 7.7 | 7.8 | 8 |
| turbidity after aging (NTU) | 4.1 | 2.6 | 2.8 | 247.4 | >1000 | >1000 |

The precipitates formed in the 8×, 16× and 32× diluted solutions are collected by centrifugation and identified as crystalline ZnO by PXRD. From the supernatant, a single crystal is grown and shown by X-ray diffraction to be Lysine Monohydrochloride Dihydrate (Lysine.HCl.2H$_2$O). These data indicate that the ZLC complex disassociates upon dilution, with consequent precipitation of zinc oxide.

The mechanism of the ZLC hydrolysis reaction can be expressed as

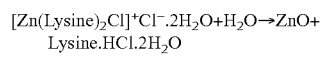$+H_2O \rightarrow ZnO + $ Lysine.HCl.2H$_2$O

In an underarm product, a mixture of ZnO+lysine HCl, in the presence of sweat, will form ZLC, which will enter the sweat duct and form a plug of ZnO.

Flocculation: Another mechanism by which the ZLC blocks sweat release involves flocculation of ZLC in the presence of protein. Bovine Serum Albumin (BSA) is used as the protein in this study. Control solution (DI water) and three 1% BSA aqueous solutions with different pH are prepared as set forth on Table 2.

TABLE 2

|  | sample 1 | sample 2 | sample 3 |
|---|---|---|---|
| H$_2$O | 15 ml | 15 ml | 15 ml |
| BSA | 0 g | 155.1 mg | 155.2 mg |
| % BSA w/w | 0% | 1% | 1% |
| pH | 6.4 | 7.2 | adjusted to 5.1 |
| Turbidity (NTU) | 0.35 | 3.6 | 10.6 |
| Observation | Transparent | Transparent | Transparent |

ZLC powder is added to the above samples to study the interaction between ZLC and BSA and to determine whether ZLC has astringent properties, i.e., whether it can form a precipitate and thus behave as an antiperspirant. Turbidity and pH of solutions are measured 5 hours after the mixtures were placed in a 37° C. oven, and the results are shown in Table 3.

TABLE 3

|  | sample 1 | sample 2 | sample 3 |
|---|---|---|---|
| ZLC added | 151.1 mg | 151.1 mg | 150.9 mg |
| ZLC concentration in solution | about 0.98% w/w or 15 mg/ml | about 0.96% w/w or 15 mg/ml | about 0.96% w/w or 15 mg/ml |
| observation | transparent solution becomes slightly cloudy | a lot white precipitate formed, solution becomes very cloudy | a lot white precipitate formed, solution becomes very cloudy |

TABLE 3-continued

|  | sample 1 | sample 2 | sample 3 |
|---|---|---|---|
| pH | 8 | 8.2 | 8 |
| Turbidity (NTU) | 357 | >1000 | >1000 |

Thus, in the sweat duct (pH=5-7), ZLC will hydrolyze to insoluble ZnO to physically block the sweat ducts. In addition, ZLC also has the ability to flocculate proteins, such as BSA, in the sweat, thus enhancing the formation of "plugs" in the sweat ducts, As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The invention claimed is:

1. An oral care composition for application to the oral cavity which comprises the zinc-lysine complex having a formula $[Zn(C_6H_{14}N_2O_2)_2Cl]^+Cl^-$, optionally in the form of a hydrate, in combination with an orally acceptable carrier; wherein the complex has a structure wherein the Zn cation is coordinated by two lysine ligands with two nitrogen atoms from alpha $NH_2$ groups of the two lysine ligands and two oxygen atoms from carboxylic groups of the two lysine ligands in an equatorial plane, having a distorted square-pyramidal geometry with the apical position occupied by a chlorine atom, to form a positive cation moiety, with which a chloride anion is combined to form an ionic salt, and wherein the complex has a powder X-ray diffraction pattern substantially corresponding to one of the two patterns depicted in FIG. 1.

2. The composition of claim 1, wherein the zinc-lysine complex is in crystalline form.

3. The composition according to claim 1, wherein the zinc-lysine complex is in the form of a hydrate.

4. The composition according to claims 1, wherein the zinc-lysine complex is in the form of a hydrate having the formula $[Zn(Lysine)_2Cl]^+Cl^-\cdot 2H_2O$.

5. The composition according to claims 1, wherein the zinc-lysine complex is in the form of approximately cubic crystals.

6. The composition of claim 1 wherein the zinc-lysine complex is formed in situ from zinc oxide and lysine hydrochloride.

7. The composition of claim 1 which provides a zinc oxide precipitate upon dilution with water.

8. The composition of claim 1 comprising the zinc-lysine complex in an amount of 0.05 to 40% by weight of the composition.

9. The composition of claim 1 comprising a total amount of zinc of 0.05 to 10% by weight.

10. The composition of claim 1 wherein the carrier comprises less than 10% water, optionally less than 5%, or is anhydrous.

11. The oral care composition of claim 1 wherein the composition is a toothpaste, dentifrice, or mouthwash.

* * * * *